United States Patent [19]
Whitmire

[11] Patent Number: 6,120,806
[45] Date of Patent: Sep. 19, 2000

[54] ORAL FORMULATIONS FOR CONTROLLED RELEASE OF ALCOHOL DETERRENTS

[76] Inventor: David R. Whitmire, P.O. Box 393, Watkinsville, Ga. 30677-0393

[21] Appl. No.: 08/882,176

[22] Filed: Jun. 25, 1997

[51] Int. Cl.⁷ .............................. A61K 9/16; A61K 47/32; A61P 25/32
[52] U.S. Cl. .......................... 424/497; 424/499; 514/811
[58] Field of Search ..................................... 424/486–488, 424/494, 497, 499–501, 461–62, 469, 426; 514/952, 811

[56] References Cited

U.S. PATENT DOCUMENTS

| | | |
|---|---|---|
| 4,011,061 | 3/1977 | Forseen et al. . |
| 4,329,332 | 5/1982 | Couvreur et al. . |
| 4,394,149 | 7/1983 | Szoka, Jr. et al. . |
| 4,489,055 | 12/1984 | Couvreur et al. . |
| 4,622,244 | 11/1986 | Lapka et al. . |

(List continued on next page.)

FOREIGN PATENT DOCUMENTS

| | | |
|---|---|---|
| 32 34 309 | 3/1984 | Germany . |
| WO 89/09208 | 10/1989 | WIPO . |
| WO 92/19266 | 11/1992 | WIPO . |

OTHER PUBLICATIONS

Kuzma, et al., "Subcutaneous hydrogels reservoir system for controlled drug delivery," *Macromol. Symposium* 109: 15–26 (1995).

Benita, S., et al., "Characterization of Drug–Loaded Poly(*d, l*–lactide) Microspheres" *J. Pharmaceutical Sciences* 73(12):1721–1724 (1984).

Bruguera, M., et al., "Hepatic Disease Associated With Ground–Glass Inclusions in Hepatocytes After Cyanamide Therapy" *Arch. Pathol. Lab. Med.* 110:906–910 (1986).

Jalil, R., et al., "Biodegradable poly(lactic acid) and poly-(lactide–co–glycolide) microcapsules: problems associated with preparative techniques and release properties" Microencapsulation 7(3):297–325 (1990).

Kupari, M., et al., "Possible Cardiovascular Hazards of the Alcohol–Calcium Carbimide Interaction" *J. Toxicol.–Clin. Toxicol.* 19(1):79–86 (1982).

Lim, F., et al., "Microencapsulation of Living Cells and Tissues" *J. Pharmaceutical Sciences* 70(4):351–353 (1981).

Mathiowitz, E., et al., "Morphology of Polyanhydride Microsphere Delivery Systems" *Scanning Microscopy* 4(2):329–340 (1990).

Peachey, J., et al., "Calcium Carbimide in Alcoholism Treatment. Part 2: medical findings of a short–term, placebo–controlled, double–blind clinical trial" *British J. of Addiction* 84:1359–1366 (1989).

Rodger, W., "Hazards of Calcium Carbimide ("Abstem")" *British Medical Journal*, p. 989 (Oct. 13, 1962).

(List continued on next page.)

*Primary Examiner*—Edward J. Webman
*Attorney, Agent, or Firm*—Arnall Golden & Gregory, LLP

[57] ABSTRACT

An oral controlled release dosage form for cyanamide whereby a portion of a cyanamide dose administered to a patient remains transiently partitioned within encapsulating material, thereby retarding metabolism of the total administered cyanamide dose, is described. No investigator has reported the use of dosage forms enabling controlled release of cyanamide. The preparation, when administered to ethanol metabolizing individuals, can elevate blood acetaldehyde to such levels, and for such periods of time, that the individuals will be deterred from future alcohol consumption. The controlled release of cyanamide provides an optimal time-profile of alcohol deterrence specific for individual patients. The formulation avoids the side-effects associated with the relatively high concentrations of cyanamide and cyanamide-metabolites, and the attendant untoward toxic effects, caused by a typical bolus cyanamide dose, thereby attenuating the intensity of the sickness caused by acetaldehyde, and increasing patient compliance with cyanamide therapy.

16 Claims, 1 Drawing Sheet

U.S. PATENT DOCUMENTS

| | | |
|---|---|---|
| 4,678,809 | 7/1987 | Phillips . |
| 4,726,941 | 2/1988 | Nagasawa et al. . |
| 4,913,908 | 4/1990 | Couvreur et al. . |
| 5,486,362 | 1/1996 | Kitchell et al. . |
| 5,641,515 | 6/1997 | Ramtoola . |
| 5,662,938 | 9/1997 | Vert et al. . |

OTHER PUBLICATIONS

Thomsen, P., et al., "Ground glass inclusions in liver cells in an alcoholic treated with cyanamide (Dispan)" *Liver* 1:67–73 (1981).

Vazquez, J., et al., "Cyanamide–induced liver injury. A predictable lesion" *Liver* 3:225–230 (1983).

Vazquez, J., et al., "Hepatitis Induced by Drugs Used as Alcohol Aversion Therapy" *Diagnostic Histopathology* 6:29–37 (1983).

FIG. 1

ORAL FORMULATIONS FOR CONTROLLED RELEASE OF ALCOHOL DETERRENTS

FIELD OF THE INVENTION

This invention relates to controlled release of drugs, specifically to controlled release of cyanamide, and in the preferred embodiment, controlled release from cyanamide-containing polymerized alkyl cyanoacrylate particles.

BACKGROUND OF THE INVENTION

Social Impact of Alcohol Abuse

Alcohol abuse and alcohol dependence (i.e., alcoholism) are serious public health problems of modem society. In the United States alone, an estimated 13 million adults exhibit symptoms of alcohol dependence due to excessive alcohol intake, and an additional 7 million abuse alcohol without showing symptoms of dependence according to U.S. Government projections. Alcohol dependence and abuse are very expensive: in economic and medical terms, they cost the U.S. well over $200 billion in 1991 with no prospect of falling or leveling off. The social and psychological damages inflicted on individuals as a consequence of alcohol abuse, e.g., children born with fetal alcohol syndrome (FAS) and victims of alcohol-related accidental death, homicide, suicide, etc., are immense.

While it is generally accepted that alcoholism and alcohol abuse are afflictions with staggering international economic, social, medical, and psychological repercussions, success in preventing or otherwise ameliorating the consequences of these problems has been an elusive goal. Only very recently the public view that alcoholism and alcohol abuse are remediable solely by moral imperatives has been changed to include an awareness of alcoholism and alcohol abuse as physiological aberrations whose etiology may be understood and for which therapy may be found through scientific pursuits. Both alcohol abuse and dependence arise as a result of different, complex, and as yet incompletely understood processes. At present, alcohol research is well in the mainstream of scientific efforts.

Pharmacotherapy of Alcohol Abuse

Two important and related goals in pharmacotherapy of alcohol abuse are (1) to reduce alcohol consumption, and (2) to treat co-morbid psychiatric disorders. Essential components of pharmacotherapy include determination of: the optimal therapeutic dose, the minimum effective dose, and the maximum tolerated dose. Latent metabolic effects of chronic, variable-term alcohol abuse, along with intersubject variability must be considered. Therapeutic preparations to reduce alcohol use can be classified as (1) centrally-acting antagonists which prevent or reverse alcohol intoxication without reducing blood alcohol concentration, (2) amethystic agents which directly reduce blood-alcohol concentration, (3) antidipsotropic drugs which associate negative feedback with alcohol drinking, and (4) drugs which tend to attenuate alcohol-craving such as naltrexone, among others.

Antidipsotropic Drugs

The only two pharmaceuticals currently used as alcohol-sensitizing drugs, disulfiram and cyanamide, are both chemically reactive species and non-specific enzyme inhibitors. The alcohol sensitizing drugs disulfiram (tetraethylthiuram disulfide; Antabuse™), and cyanamide in various forms (citrated calcium carbimide; Temposil™) increase blood acetaldehyde concentrations in the presence of ethanol oxidation by inhibiting the oxidation of acetaldehyde to acetic acid, thereby producing physiological effects that deter further alcohol use. The fundamental mechanism for the alcohol-deterrent action of disulfiram and cyanamide is thought to be inhibition of hepatic acetaldehyde dehydrogenase enzymes (ALDH). Drinking alcohol after ALDH inhibition can increase a subject's acetaldehyde concentration by several-fold greater than the acetaldehyde concentration achieved by alcohol-drinking with no ALDH inhibition. Acetaldehyde concentrations so achieved tend to cause intense sickness in the alcohol-drinker. The intense sickness associates negative-feedback with alcohol consumption, thereby conditioning alcohol-drinkers to become alcohol-averse. After decades of testing and use, disulfiram and cyanamide have been demonstrated to have variable toxic effects along with variable effectiveness in causing alcohol aversion Disulfiram Chemical Properfies Disulfiram (tetraethylthiuram disulfide) was first proposed as an aversive agent for the treatment of alcoholism by Williams (Williams, 1937, JAMA 109:1472–1473). Williams noticed that workers in the rubber industry who had been exposed to thiuram compounds, used as accelerators of vulcanization, experienced unpleasant effects after alcohol consumption. Disulfiram has been approved for use as a drug since 1948. Disulfiram is a general reagent for determination of SH groups in proteins (Neims et al., 1966, J. Biol. Chem. 241, pp. 3036–3040), and reacts with thiols to form diethylammonium diethyldithiocarbamates, carbon disulfide and disulfide derived from thiol groups (Coffey, supra, pp. 331–332). Disulfiram also undergoes disulfide exchange reactions under mild conditions.

Disulfiram Biological Properties

Given its chemical properties, it is not surprising to find that disulfiram is a broadly acting, non-specific inhibitor of many physiologically important sulfhydryl-containing compounds including enzymes. (Wright and Moore, 1990, Am. J. Medicine, 88:647–655); (for a review, see Banys, 1988, supra). Thus, disulfiram inhibits enzymes critical in neurotransmitter metabolism (dopamine-$\beta$-hydroxylase, DBH), drug metabolism and detoxification (microsomal mixed function oxidases), and multiple pathways of intermediary metabolism. It is a potent inhibitor of many liver enzymes, including ALDH, DBH, aniline hydroxylase, nicotinamide-adenine dinucleotide phosphate (NADPH) oxidase, and cytochrome P-450. Other studies have demonstrated inhibition of glyceraldehyde-3-phosphate dehydrogenase, succinic dehydrogenase, xanthine oxidase, hexokinase, and NADPH dehydrogenase. Still other studies have established inhibition of superoxide dismutase, which is thought to be an important antioxidant defense mechanism against free radical-induced biological damage. The details of these and other instances of enzyme inhibition may be found in the references cited in Banys, 1988, supra. Disulfiram's lack of specificity clearly contributes to and may be largely responsible for the substantial toxicity that accompanies the therapeutic use of disulfiram.

In vitro, disulfiram (Pietruszko, 1989, supra) is a potent inhibitor of the high Km cytosolic isozyme (ALDH-II) but inhibits the major acetaldehyde oxidizing mitochondrial isozyme (ALDH-I) only slightly. However, under conditions where trace amounts of certain mercaptans such as 2-mercaptoethanol or the in vivo metabolite methanethiol are added to disulfiram to generate a mixed disulfide, the low Km mitochondrial ALDH-I isozyme, normally resistant to disulfiram, is inactivated. Thus, disulfiram directly inhibits ALDH-II, but only indirectly inhibits ALDH-I via metabolites (Pietruszko, 1989, supra).

In vivo, disulfiram acts slowly to inhibit ALDH over 12 hours, and this inhibition is irreversible (Pietruszko, 1989, supra). Restoration of ALDH activity after disulfiram administration depends upon de novo enzyme synthesis of ALDH, which requires six or more days. Thus, disulfiram and its metabolites have the capacity to shut down hepatic acetaldehyde oxidation via ALDH-I and ALDH-II so that in the presence of ethanol metabolism, abnormally high levels of acetaldehyde will rapidly accumulate. Although exogenous acetaldehyde is known to be toxic, it is not at all clear that endogenous accumulation of acetaldehyde is the only or even the main causative agent in the so-called disulfiram-alcohol reaction (DAR) described below. The direct involvement of acetaldehyde in any of the manifestations of alcohol intolerance is poorly studied, poorly understood and remains unproven.

Disulfiram: Clinical Use and Toxicity

Disulfiram, marketed by Wyeth-Ayerst as Antabuse™, is essentially the only alcohol-sensitizing or alcohol-deterrent agent approved for use in the U.S. In a patient metabolizing ethanol, inhibition of ALDH by disulfiram produces the characteristic DAR comprising highly unpleasant physiological reactions including flushing, tachypnoea, palpitations, nausea and tachycardia (Peachey and Naranjo, 1985, Medical Progress, May:45–59). The rationale for treatment with disulfiram is that fear of these reactions will deter alcoholics from further drinking (Peachey and Naranjo, 1985, supra).

As described in the 1996 Physician's Desk Reference (Medical Economics Co., Oradell, N.J., pp. 2358–59), Antabuse™, when given to alcohol metabolizing subjects, produces flushing, throbbing in the head and neck, throbbing headache pain, respiratory difficulty, nausea, copious vomiting, sweating, thirst, chest pain, palpitation, dyspnea, hyperventilation, tachycardia, hypotension, syncope, marked uneasiness, weakness, vertigo, blurred vision, and confusion (Physician's Desk Reference, 1991, supra).

Significant cardiac, hepatic, and neurological toxicity, have been observed in patients enduring disulfiram therapy. For example, in severe reactions to Antabuse™, there may be respiratory depression, cardiovascular collapse, arrhythmias, myocardial infarction, acute congestive heart failure, unconsciousness, convulsions, and death (see Physician's Desk Reference, supra). These undesirable side effects have been attributed to inhibition of enzymes other than ALDHs, as well as inhibition of the normal physiological functions of one or more of the ALDHs. In fact, many clinicians consider the health risks of disulfiram to be so great, that they refuse to use disulfiram therapy for alcohol abuse. Moreover, many patients either refuse disulfiram therapy or abandon its use. Thus, the art has not yet been provided with a drug for the selective or direct reversible inhibition of ALDH-I without the undesirable side effects or toxicity which accompanies disulfiram treatment.

Placebo-controlled clinical trials of Antabuse™ (disulfiram) (Fuller et al., 1986, JAMA 256:1449–1455; Fuller and Roth, 1979, Ann. Int. Med. 90:901–904) have shown that disulfiram is no more effective than placebo controls in reducing alcohol consumption, when compared with pre-treatment levels. According to Banys (Banys, 1988, supra), even though millions of doses of disulfiram have been prescribed for the treatment of alcoholism since 1948, well-controlled studies have never demonstrated that disulfiram is more effective than placebo controls in producing sustained abstinence. Many of the studies published since 1948 suffer from serious flaws. In reviewing the efficacy of disulfiram, Banys (Banys, 1988, supra) supports the contention of Sellers, et al (Sellers et al, 1981, N. Eng. J. Med. 305:1255–1262), that evidence supporting the efficacy of disulfiram is limited. Controlled clinical trials of efficacy show no improvement or short-term improvement only. Appreciable improvements in abstinence and improved social functioning reported by chronic alcoholics during the first three months of treatment with therapeutic (250 mg daily) and sub-therapeutic doses (1 mg daily) of disulfiram, probably result from non-specific, nonpharmacologic drug activity. The subsequent decline from early improvement after the first three months of treatment, probably reflects both the low potency of the drug and the increased importance of non-pharmacologic factors as determinants of long-term outcomes of treatment.

In accord with this, of all the numerous studies of disulfiram, according to Peachey et al (Peachey et al (a), 1989, Brit. J. Addict. 84:877–887), only two properly controlled clinical trials of disulfiram therapy have been conducted, with both concluding that disulfiram was no more effective than placebo controls in bringing about continued, long-term abstinence in alcoholic patients. Thus, the weight of the evidence after more than fifty years of use is that disulfiram is toxic, unsafe and ineffective.

Cyanamide Chemical Properties

The citrated calcium salt of cyanamide resulted from a search for an alcohol-sensitizing agent less toxic than disulfiram (Ferguson, 1956, Canad. M. A. J., 74:793–795; Reilly, 1976, Lancet, Apr. 24, 1976: 911–912), but even now only disulfiram has been approved for use in the United States. Citrated calcium cyanamide is hydrolyzed to free cyanamide ($H_2NCN$) in aqueous solution, hence the general properties of cyanamide are relevant. Like disulfiram, cyanamide's alcohol-sensitizing effect was discovered among industrial workers exposed to the substance in the workplace. Although chemically distinct from disulfiram, it is also a reactive species. Cyanamide, which readily forms compounds by addition to the cyano group, yields guanidinium compounds, O-alkylisoureas, and S-alkylisothioureas when reacted with alkyl amines, alcohols and thiols, respectively (Rodd's Chemistry of Carbon Compounds, 1965, Vol. 1, Part C, Coffey, ed., Elsevier, Amsterdam, p.374), (i.e., with nucleophilic functionalities present in proteins). Cyanamide is sufficiently reactive that at slightly alkaline pH it dimerizes to cyanoguanidine, a species that is itself reactive toward nucleophiles (e.g., alkyl amines) (Rodd, 1965, supra, p. 349). Incorporation of citrate in the pharmaceutical formulation provides the slightly acid pH required for stability with respect to dimerization.

Cyanamide Biological Properties

Neither ALDH-I (the low Km isozyme) nor ALDH-II (the high Km isozyme) are inhibited in vitro by cyanamide, but in vivo a reactive product of cyanamide metabolism inhibits both isozymes (Deitrich et al., 1976, Biochem. Pharmacol. 25:2733–2737; DeMaster et al., 1982, Biochem. Biophys. Res. Comm. 107:1333–1339). Formation of this active inhibitor was shown initially to be catalyzed by enzyme(s) present in intact mitochondria and the microsomal fraction of rat liver (DeMaster et al, 1983, Pharmacol. Biochem. Behav. 18 (Supp. 1): 273–277). Mitochondrial catalase has been shown to activate cyanamide to an ALDH inhibitor (DeMaster et al, 1984, Biochem. Biophys. Res. Comm. 122:358–365; Svanas and Weiner, 1985, Biochem. Pharmacol. 34:1197–1204). Further, Shirota et al, (Shirota et al(a), 1987, Alcohol & Alcoholism Supp. 1:219–223 and Shirota et al (b), 1987, Toxicol. Let. 37:7–12), showed that cyanamide inhibits ALDH via a reactive species and that cyanide is generated as a product of cyanamide oxidation by catalase under conditions in which the ALDH inhibitory species is also generated. According to Shirota et al, (Shirota et al.(b), 1987, supra), this cyanide formation could serve as a basis for cyanamide toxicity in vivo. It was postulated in 1987 (Shirota et al.(b), 1987, supra) that the oxidation of cyanamide would yield nitroxyl (HNO) as a product and that this highly reactive species is the active ALDH inhibitor. In 1990, Nagasawa et al (Nagasawa et al, J. Med. Chem. 33:3120–3122) presented evidence, via isotope tracer experiments, that nitroxyl was formed in the catalase-mediated bioactivation of cyanamide. They suggested that their data and those of others support nitroxyl as the active ALDH inhibitor, noting that millimolar concentrations of cyanide do not inhibit ALDH. Marchner and Tottmar (Marchner and Tottmar, 1978, Acta Pharmacol. et Toxicol. 43: 219), reported that inhibition of ALDH with cyanamide is maximal at 1–2 hours after drug administration, and is reversible, with restoration of 80% of the ALDH activity occurring within 24 hours.

Cyanamide: Clinical Use and Toxicity

Absorption of calcium carbimide (i.e. the calcium salt of cyanamide) following oral administration is extremely rapid, causing nausea, headache and vomiting in the presence of ethanol metabolism. In an attempt to reduce the rate of absorption, calcium carbimide has been formulated as a slow release tablet. To prevent its decomposition to ammonia, cyanamide is prepared in the citrated form (one part cyanamide to two parts citric acid). In the gastric environment, calcium carbimide is hydrolyzed to carbimide (cyanamide, $H_2NCN$) which is rapidly absorbed into the portal circulation. Data from animal experiments indicate that cyanamide is rapidly absorbed, metabolized and eliminated, and in view of the rapid onset and short duration of the calcium carbimide-ethanol reaction (CER), it is likely that absorption, metabolism and elimination are also rapid in humans. At least 94% of cyanamide is eliminated within six hours via this route by the rat. In Canada and other countries, calcium carbimide has not been widely used because of its short duration of activity. This is due to its facile conversion in vivo to an acetylated derivative, viz. acetylcyanamide (AC), which is rapidly excreted in the urine. Like cyanamide, AC is devoid of ALDH inhibitory activity in vitro.

As with disulfiram, cyanamide has been used in alcohol-aversion and psychological deterrence therapy as described above (Peachey and Naranjo, 1985, supra). Peachey speculated that one reason cyanamide has not yet been approved for use in the United States is because of its suspected antithyroid activity in experimental animals (Peachey, 1981, J. Clin. Psychopharmacol. 1:368–375). However, cyanamide has been used safely for decades in patients with no pre-existing thyroid dysfunction. Citrated calcium cyanamide is marketed variously as Temposil™, Dipsan™ and Abstem™ (Shirota et al.(a), 1987, supra) while Aplain cyanamide, marketed as Colme™, is commonly used in Spain (Valerdiz and Vazquez, 1989, Appl. Pathol. 7:344–349).

Cyanamide, like disulfiram is reported to be associated with medical complications. Fewer side effects have been reported with cyanamide than with disulfiram, There are few contraindications to treatment with cyanamide. Toxic effects reported for cyanamide include: (i) allergic contact dermatitis (Conde-Salazar et al., 1981, Contact Dermatitis 7:329–330 and references cited therein), and peripheral neuropathy (Reilly, 1976, supra); (ii) liver injury, including generation of Aground-glass inclusion bodies in liver cells of alcoholics treated with cyanamide (Vazquez et al (a), 1983, Diagnostic Histopath. 6:29–37) first reported by Vazquez and Cervera (Vazquez and Cervera, 1980, Lancet:361–362) using plain cyanamide, and by Thomsen and Reinicke (Thomsen and Reinicke, 1981, Liver 1:67–73) as well as Koyama et al (Koyama et al., 1984, Acta Hepatol. Jpn. 25:251–256) using the citrated calcium salt of cyanamide; a series of reports of hepatotoxicity, including "ground-glass" inclusions, inflammatory reactions associated with liver cell destruction, portal tract fibrosis, scarring, even cirrhosis according to the above-cited references and Vazquez et al (Vazquez et al.(a), 1983, supra; Vazquez et al.(b), 1983, Liver 3:225–230; Bruguera et al., 1986, Arch. Pathol. Lab. Med. 110:906–910; Bruguera et al., 1987, Liver 7:216–222; Valerdiz and Vazquez, 1989, supra), for cyanamide and disulfiram, but not calcium cyanamide; and (iii) cardiotoxic effects, including hypotension and even cardiac death according to Rodger (Rodger, 1962, Br. Med. J. 2:989), and hazardous cardioacceleration according to Kupari et al (Kupari et al., 1982, J. Toxicol.—Clin. Toxicol. 19:79–86); Kupari et al (Kupari et al., 1982, supra) suggested that the use of alcohol aversive drugs including disulfiram and cyanamide has been contraindicated to patients with known cardiac diseases, but pointed out that it is common that asymptomatic chronic alcoholics have a number of cardiac problems. Clearly, use of cyanamide as cited above may be hazardous. However, many of cyanamide's toxic side effects cited above may have been confounded by the presence of elevated blood-acetaldehyde concentrations caused by the cyanamide-ethanol reaction.

Peachey et al (Peachey et al.(b), 1989, Brit. J. Addict. 84:1359–1366), conducted the only placebo-controlled, double-blind clinical trial of Temposil™. Based on this trial, Peachey and his colleagues concluded that this cyanamide was safe for use in alcoholics with normal thyroid function and without other serious medical conditions. Thyroid function was not altered during the Temposil™ trial, except for a single patient who entered the trial with sub-normal baseline thyroid function; thus it was concluded that cyanamide was safe for short-term use in alcoholics with without pre-existing thyroid dysfunction. Peachey et al (Peachey et al.(a), 1989, supra), reported that they observed no hepatotoxicity related to cyanamide therapy. The effects of long-term treatment with cyanamide in controlled studies remains unknown.

According to Peachey (Peachey, 1981, supra), in Canada and other countries where cyanamide is approved for safety and efficacy, cyanamide has not been widely used because of its short duration of alcohol-deterrent activity. Peachey et al, (Peachey et al.(a), 1989, supra; Peachey et al.(b), 1989, supra), reported that, compared with pre-treatment levels, cyanamide was no more effective than placebo controls in reducing alcohol consumption. Some reports indicate that use of either disulfiram or cyanamide is counterproductive in treatment of alcoholism. Brien et al (Brien et al., 1980, Eur. J. Clin. Pharmacol. 18:199–205), reported that results from male alcoholic volunteers who ingested small amounts of ethanol after oral administration of cyanamide, supported anecdotal evidence from alcoholics, who state that they can circumvent a severe cyanamide-ethanol reaction by ingesting small amounts of ethanol over a few hours, and thereafter drink excessively with impunity. If cyanamide can be effectively "burned-off" by slow alcohol ingestion for a period followed by excessive consumption, the effectiveness of cyanamide as an anti-alcohol drug appears to be limited.

The variable results of cyanamide's alcohol-deterrent effects as reported above, can likely be explained by considering:

(1) aldehyde dehydrogenase activities within the general population are variable, the precise mechanism by which cyanamide exerts its alcohol-deterrent effects is not well understood, (2) the severity of the cyanamide-alcohol reaction leads to poor patient compliance with the pharmaco-therapeutic protocol, (3) cyanamide and related metabolites are water soluble, have a relatively short half-life, and are rapidly cleared via the kidneys.

Thus, it is clear that detecting and measuring cyanamide's alcohol-deterrent-effects can be confounded. However, cyanamide's property of elevating acetaldehyde associated with alcohol-drinking which, in turn results in intense sickness and attenuation of alcohol-drinking, has been demonstrated unequivocally.

The severity of problems caused by alcoholism (alcohol dependence) and alcohol abuse, along with the attendant social and economic costs are immense and well documented and have motivated much research to ameliorate these problems. Numerous pharmacotherapies have been evaluated either as isolated treatment options, or as part of broader support programs (e.g. counseling, Alcoholics Anonymous, etc.).

SUMMARY OF THE INVENTION

An oral controlled release dosage form for cyanamide whereby a portion of a cyanamide dose administered to a patient remains transiently partitioned within encapsulating material, thereby retarding metabolism of the total administered cyanamide dose, is described. No investigator has reported the use of dosage forms enabling controlled release of cyanamide. The preparation, when administered to ethanol metabolizing individuals, can elevate blood acetaldehyde to such levels, and for such periods of time, that the individuals will be deterred from future alcohol consumption. The controlled release of cyanamide provides an optimal time-profile of alcohol deterrence specific for individual patients. The formulation avoids the side-effects associated with the relatively high concentrations of cyanamide and cyanamide-metabolites, and the attendant untoward toxic effects, caused by a typical bolus cyanamide dose, thereby attenuating the intensity of the sickness caused by acetaldehyde, and increasing patient compliance with cyanamide therapy.

DETAILED DESCRIPTION OF THE INVENTION

An oral formulation, and method of use, of encapsulated cyanamide, or related anti-alcohol drugs, as a controlled release dosage form is described. The encapsulated cyanamide is administered to a patient in need thereof as a therapy for alcohol dependence (alcoholism) or alcohol abuse. The method is therapeutic for alcohol dependence and alcohol abuse because it results in unpleasant symptoms when administered to an ethanol-metabolizing individual. The method is particularly useful as part of a broader therapeutic program which includes psychological counseling, peer-support (e.g. Alcoholics Anonymous), and pharmacotherapy with additional drug species (e.g. naltrexone) to attenuate alcohol-craving.

Drugs Which are Encapsulated

Cyanamide

Since 1972 cyanamide has been the subject of more than two-hundred in vitro and in vivo studies. Some of these studies attempted to evaluate cyanamide's alcohol deterrent effects but many of the studies were not controlled or poorly controlled relative to the metabolism of alcohol, acetaldehyde, and cyanamide in human subjects. No study has reported "titrating" patients with cyanamide as one means of controlling for potentially confounding results caused by inter-subject variability in alcohol metabolism, acetaldehyde metabolism, and cyanamide metabolism. Titration of patients with cyanamide requires dosage forms which enable controlled release of cyanamide, but no investigator has reported the use of dosage forms enabling controlled release of cyanamide. Nagasawa et. al. demonstrated that several acylated cyanamide compounds elevated blood acetaldehyde concentrations in rats for a longer period of time than did cyanamide (Nagasawa-H-T; Kwon-C-H; DeMaster-E-G; Shirota-F-N. Prodrugs of cyanamide as (long-acting) alcohol deterrent agents. Biochemical Pharmacology, 35(2):129–132, 1986; U.S. Pat. No. 4,726, 941). Kitchell et. al. suggested that particles with dimensions in the range of 38 $\mu$m–250 $\mu$m, containing citrated calcium cyanamide, could be used as a controlled, sustained release injectable dosage form for alcohol dependency (U.S. Pat. No. 5,486,362). These forms of the drug are useful in the formulations described herein, using dosages extrapolated from approved concentrations and drug-blood profiles over time using standard methodology.

Naltrexone

In 1994, the FDA approved the use of naltrexone (i.e. Trexan™, ReVia™) as a pharmacotherapy to reduce alcohol-craving. Naltrexone is an opiate antagonist which, at a molecular level, binds to opiate receptors in the brains of humans and experimental laboratory animals. Since no receptor for alcohol has ever been discovered, the precise mechanism by which naltrexone reduces alcohol-craving is not well understood. However, in numerous studies, it has been demonstrated that naltrexone has the capability to reduce alcohol-craving and alcohol-consumption in humans and animals, thereby increasing abstinence from alcohol use.

In general, naltrexone therapy is more effective in reducing alcohol-use when it is used as part of a broader therapeutic program which includes counseling. Although naltrexone is effective in reducing alcohol use in a general population of alcohol users, naltrexone is more effective in sub-populations of alcohol users who are motivated to remain abstinent; in general, as patient motivation toward abstinence increases, the effectiveness of naltrexone therapy increases. The synergism of naltrexone combined with other support therapy has prompted some researchers to recommend investigation of combination drug therapies using naltrexone and disulfuram (Howard, M. O.; McGuffin, R. W.; Saxon, A. J.; Sloan, K. L.; Walker, R. D. Clinical issues related to the costs of alcoholism. PharmacoEconomics, 9(2):134–145, 1996.) Similarly, Kwentus and Sheffel reported in their review that disulfiram is no longer used as an alcohol abuse treatment by itself, but as an adjunct to a general program of therapy (Kwentus, J. and Sheffel, W. Use of disulfiram and naltrexone. In: W. D. Lerner and M. A. Barr (Eds.), Handbook of Hospital Based Substance Abuse Treatment, New York: Pergamon Press, 1990. 218 p (pp 154–168). These recommendations must be tempered, however, with the fact that naltrexone and disulfiram are both hepatotoxic. One report stated unequivocally that use of (naltrexone) with disulfiram is not recommended because of potential hepatotoxic involvement (Medical Letter on Drugs and Therapeutics, 37(953):64–66, 1995). Based on the numerous reports indicating that naltrexone is more effective in association with other therapies, it is somewhat striking that no investigation has been reported which evaluated the potential benefits of a combination therapy using naltrexone and cyanamide. The reported short duration of cyanamide's alcohol deterrent effects likely explains the lack of an investigation using naltrexone and cyanamide in combination.

This problem is overcome using a controlled release formulation of cyanamide which optionally includes naltrexone in an effective amount to obtain alcohol abstinence by the patient.

Encapsulation Media

Controlled release is defined herein as a formulation providing release over a period of time, at least four hours, more preferably eight hours, most preferably twelve hours. Release is accompanied by uptake through the gastrointestinal stream to create an effective concentration in the blood to cause alcohol avoidance. The encapsulation media will typically be in microparticulate or nanoparticulate form, although this may actually consist of microspheres, microcapsules or irregular particles. The particles may be administered in a suspension, in a capsule, or in a tablet, which distintegrates following ingestion to release the particulates.

Microparticle preparation

Liposomes and Emulsions. Liposomes consist of a phospholipid bilayer which forms a shell around an aqueous core. Methods for preparing liposomes for administration to a patient are known to those skilled in the art; for example, U.S. Pat. No. 4,798,734 describes methods for encapsulation of biological materials in liposomes. The biological material is dissolved in a aqueous solution, and the appropriate phospholipids and lipids are added, along with surfactants if required. The material is then dialyzed or sonicated, as necessary. A review of known methods is presented by G. Gregoriadis, Chapter 14 ("Liposomes"), in *Drug Carriers in Biology and Medicine,* pp. 287–341 (Academic Press, 1979).

Polymeric Microparticles. Microspheres formed of polymers or proteins are also well known to those skilled in the art, and can be tailored for passage through the gastrointestinal tract, as described in U.S. Pat. Nos. 4,906,474, 4,925, 673, and 3,625,214, for example. There are a number of well-known methods, including solvent evaporation and coacervation/phase separation, for preparing microspheres.

Bioerodible microspheres can be prepared using any of the methods developed for making microspheres for drug delivery, as described, for example, by Mathiowitz et al., *J. Appl. Polymer Sci.* 35, 755–774(1988), and P. Deasy, in *Microencapsulation and Related Drug Processes,* pp. 61–193, (Dekker, 1984), the teachings of which are incorporated herein. The selection of a method depends on the drug properties and choice of polymer, as well as the size, external morphology, and degree of crystallinity desired, as discussed, for example, by Benita et al., J. Pharm. Sci. 73, 1721–1724 (1984), Jalil and Nixon, *J. Microencapsulation,* 7, 297–325(1990), and Mathiowitz et al., *Scanning Microscopy* 4, 329–340(1990), the teachings of which are incorporated herein.

In solvent evaporation, described, for example, in Mathiowitz et al., (1990), Benita, and U.S. Pat. No. 4,272,398 to Jaffe, the polymer is dissolved in a volatile organic solvent. The drug, either in soluble or particulate form, is added to the polymer solution and the mixture is suspended in an aqueous phase containing a surface active agent such as poly(vinyl alcohol). The resulting emulsion is stirred until most of the organic solvent evaporates, leaving solid microspheres. Microspheres of various sizes (1–1000 microns) and morphologies may be obtained by this method, which is usefull for non-labile polymers.

Coacervation/phase separation techniques have been used to encapsulate both solid and liquid core materials with various polymer coatings. U.S. Pat. Nos. 2,730,456, 2,730, 457, and 2,800,457 to Green and Schleichter, describe gelatin and gelatin-acacia (gum arabic) coating systems, for example. Simple coacervation employs a single colloid (e.g. gelatin in water) and involves the removal of the associated water from around the dispersed colloid by agents with a higher affinity for water, such as alcohols and salts. Complex coacervation employs more than one colloid, and the separation proceeds mainly by charge neutralization of the colloids carrying opposite charges rather than by dehydration. Coacervation may also be induced using nonaqueous vehicles, as described in Nakano et al., *Int. J. Pharm,* 4, 29–298(1980), for example.

Hydrogel microspheres made of gel-type polymers such as alginate or polyphosphazenes or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as illustrated, for example, by Salib, et al., *Pharmazeutische Industrie* 40–11A, 1230(1978), the teachings of which are incorporated herein. The advantage of this system is the ability to further modify the surface of the microspheres by coating them with polycationic polymers (such as polylysine) after fabrication, as described, for example, by Lim et al, *J. Pharm Sci.* 70, 351–354(1981). The microsphere particle size depends upon the extruder size as well as the polymer and gas flow rates.

Examples of polymers that can be used include polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly (isobutyl methacrylate), poly(hexylmethacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

Examples of biodegradable polymers include synthetic polymers such as polymers of lactic acid and glycolic acid, polyanhydrides, poly(ortho)esters, polyurethanes, poly (butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubbell in *Macromolecules,* 1993, 26, 581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate).

Polycyanoacrylate particles are the preferred embodiment for controlled release. The initial medical use for polycyanoacrylate was in the form of an adhesive to close surgical wounds (Physiological Tissue Adhesive Review, Methyl-2-cyanoacrylate Monomer, Bulletin from Medical Research Department, Ethicon, Inc. Arbrook, Somerville, N.J., November 1964). In 1976, Florence et al reported the first use of polymethyl alpha-cyanoacrylate and polybutyl alpha-cyanoacrylate particles as pharmaceutical dosage forms (Florence et al, Interfacial properties of polymethyl alpha-cyanoacrylate and polybutyl alpha-cyanoacrylate, J. Pharm Pharmacol, July 1976, 28:7, 539–543). In December 1978, Vezin and Florence reported the diffusion of small molecules in poly-N-alkyl cyanoacrylates which significantly broadened the applications of polyalkylcyanoacrylate particles (Vezin W. and A. Florence, Diffusion of small molecules in poly-N-alkyl cyanoacrylates, J. Pharm. Pharmacol., December 1978, 30 Suppl:, 2P). In May, 1979, Couvreur et al reported the preparation of polycyanoacrylate nanocapsules and the potential for using them as lysosomotropic carriers (Couvreur et al, Polycyanoacrylate nanocapsules as potential lysosomotropic carriers: preparation, morphological and sorptive properties, J. Pharm Pharmacol, May 1979, 31:5, 331–332). In June 1979, Florence et al, reported the preparation of biodegradable microcapsules from poly (alkyl 2-cyanoacrylate membranes (Florence et al, Potentially biodegradable microcapsules with poly (alkyl 2-cyanoacrylate) membranes, J. Pharm Pharnacol, June 1979, 31:6, 422–424). Since these early reports, Couvreur et al, have refined the preparation and use of submicroscopic particles formed of polymerized alkyl cyanoacrylate (U.S. Pat. No. 4,329,332 to Couvreur et al; U.S. Pat. No. 4,489,055 to Couvreur et al; U.S. Pat. No. 4,913,908 to Couvreur et al.).

Mechanisms which enable a controlled release dosage form relate to the physical and chemical structure of the dosage form. The preferred physical and chemical structure of the dosage form comprises polyalkylcyanoacrylate particles containing cyanamide. The preferred alkyl cyanoacrylate is one where "alkyl" denotes an alkyl radical having 1 to 12 carbon atoms. The preferred diameter of the particles is less than 600 nanometers.

To achieve particular controlled release, polyalkylcyanoacrylate particles containing cyanamide can be separately prepared from alkyl cyanoacrylate comprising only a single alkyl radical having a specific number of carbon atoms from the range of 1 to 12 carbon atoms. Particles prepared from different alkyl groups can then be combined to achieve cyanamide release specific to each alkyl group used in the preparation.

To achieve particular controlled release, polyalkylcyanoacrylate particles containing cyanamide can be separately prepared to yield particles with uniform diameters. Particles prepared to yield different uniform particle diameters can then be combined to achieve cyanamide release specific to each uniform particle diameter.

Release Modifiers

The release characteristics depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be codissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Formulations

Oral formulations. Oral formulations can consist of a suspension, solution, or emulsion, incorporating buffers, stabilizers, and enzyme inhibitors, as well as flavorings, colorings, and viscosity-modifying agents (sugars, polysaccharides such as alginate, and others are well known and approved for food and drug use). These can be encapsulated and ingested as tablets, in capsules or liquids.

Formulations for buccal or rectal administration. For administration to a mucosal membrane such as those found in the mouth, rectum, or nasopharyngeal area, it may not be necessary to provide an enteric coating. The formulation can be prepared as a porous hydrogel or other material which allows for free diffusion of drug into and out of the material, while retaining the enzymes within the formulation. This can be achieved by immobilization of the enzymes to the material or through the use of a selectively porous material. Also, bioadhesive microspheres which can adhere to mucosal membranes and increase drug retention time to the body are known to those skilled in the art and are discussed, for example, in PCT/US93/03822 by Brown University.

The method is useful for controlled release of cyanamide to accommodate the therapeutic needs of individuals. The method is useful for "titrating" individuals with cyanamide as a means to accommodate inter-subject variability in alcohol metabolism, acetaldehyde metabolism, and cyanamide metabolism. A controlled release dosage form refers to a preparation which, through one or more mechanisms, enables a portion of encapsulated cyanamide to remain transiently and particularly partitioned within the encapsulating material and thus not immediately available for metabolism.

By varying drug loading, polymer composition, particle size, and dosage amount, it appears that controlled release systems will allow establishment of any required alcohol-deterrent profile specific to an individual's particular needs.

The present invention will be further understood by reference to the following non-limiting example.

EXAMPLE 1

Controlled Release of cyanamide

Triton X-100 was added to deionized (DI) water stirring at 300 rpm, to yield a concentration of 0.5% w/v. Hydrochloric acid was added until the solution was pH 2.00. The solution was vacuum filtered using 0.45 $\mu$m filter. Ethyl-2-cyanoacrylate monomer (0.6 milliliters) was added to the filtrate over a period of eight minutes while stirring at 300 rpm. The resulting mixture was stirred overnight at 300 rpm. The solution was adjusted to pH=7.0 by addition of sodium hydroxide. The resulting suspension was vacuum filtered (2.5 $\mu$m), and 0.6 grams of cyanamide was added to the filtrate and stirred (300 rpm) for two hours. The resulting suspension was centrifuged for one hour (15,500×g, 4° C.). The supernatant was decanted and the precipitate was suspended in one milliliter of deionized (DI) water. The resulting suspension was frozen and lyophilized for a period of 72 hours.

Figure 1:
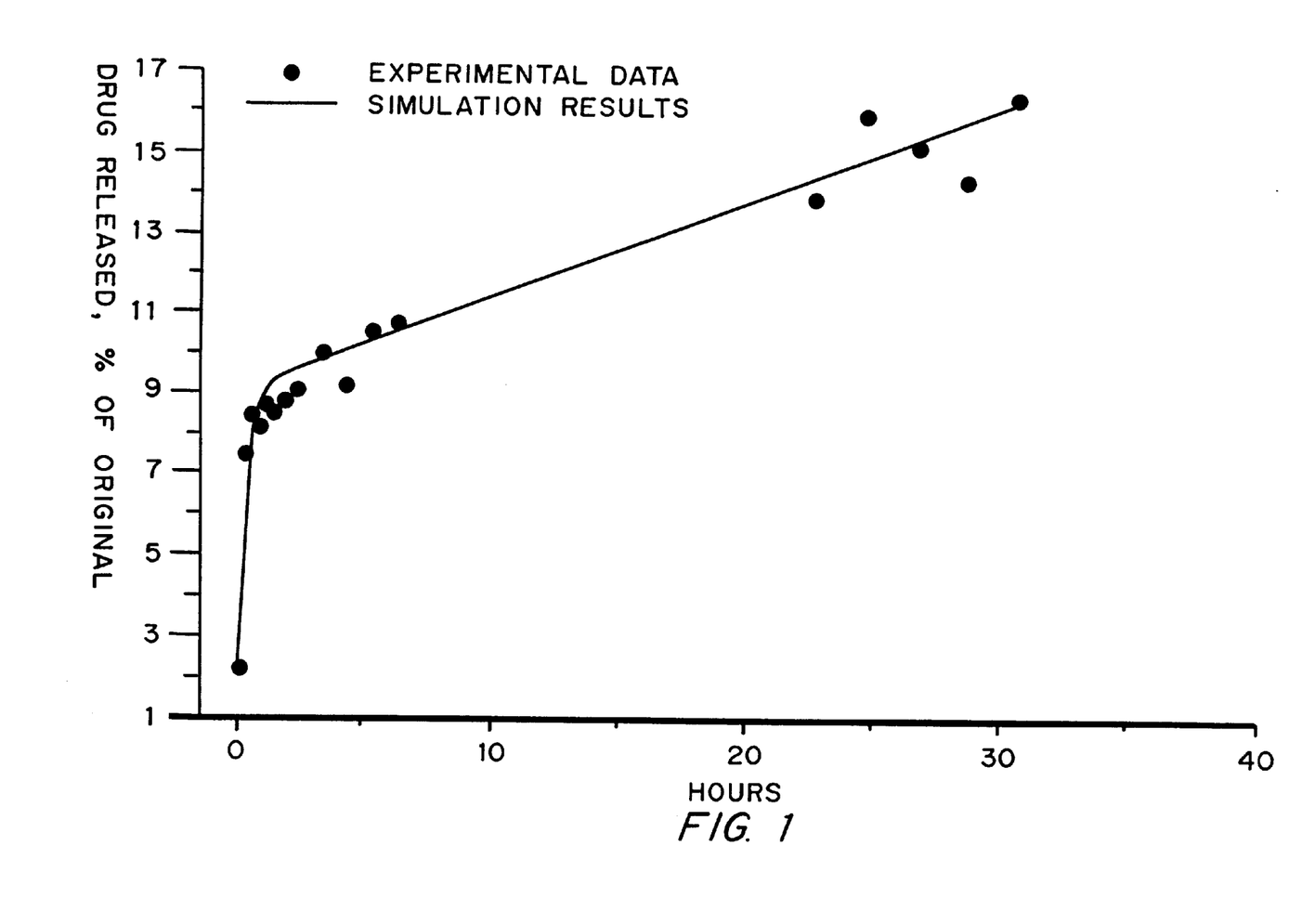
FIG. 1 shows the time course of cyanamide concentration released from polyethylene cyanoacrylate nanoparticles at pH 7 and 20° C. as a percentage of drug released over time in hours.

The lyophilized particles were added to 150 milliliters of DI water. The suspension (pH=7, 20° C.) was stirred gently for 48 hours, sampled periodically, and assayed for cyanamide concentration. The time course of cyananide released from the suspension is shown in FIG. 1. Subsequent computation indicated total cyanamide loading in the particles was 1334 micrograms, cyanamide released by initial burst was 120 micrograms, cyanamide released by diffusion from the particles was 87 micrograms, and cyanamide release from particle degradation was 10 micrograms.

Modifications and variations of the present invention will be obvious to those skilled in the art from the foregoing detailed description and references cited therein, the teachings of which are incorporated herein.

I claim:

1. A formulation for controlled release of an alcohol deterrent to a patient in need thereof comprising a cyanamide or salt thereof encapsulated in a polymeric matrix in nanoparticulate or microparticulate form releasing the deterrent in the gastrointestinal tract of the patient, and a pharmaceutically acceptable carrier for oral administration to the patient in an effective amount of the alcohol deterrent over a period of at least four hours to cause avoidance of alcohol, wherein the deterrent and matrix are encapsulated in an enteric coating.

2. The formulation of claim 1 further comprising an effective amount of naltrexone.

3. The formulation of claim 1 wherein the matrix is a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

4. The formulation of claim 1 wherein the matrix comprises release modifying agents.

5. The formulation of claim 1 wherein the polymer is polycyanoacrylate.

6. The formulation of claim 1 wherein the matrix releases in the stomach as a finction of low pH.

7. The formulation of claim 1 wherein the matrix comprises a mucosal adhesive which enhances uptake in the gastrointestinal tract.

8. A method for treating a patient in need of alcohol avoidance therapy comprising providing to the patient an effective amount of a formulation for controlled release of an alcohol deterrent to a patient in need thereof comprising a cyanamide or salt thereof encapsulated in a polymeric matrix in nanoparticulate or microparticulate form releasing the deterrent in the gastrointestinal tract of the patient, and a pharmaceutically acceptable carrier for oral administration to the patient of an effective amount of the alcohol deterrent for a period of at least four hours to cause avoidance of alcohol, wherein the deterrent and matrix are encapsulated in an enteric coating.

9. The method of claim 8 wherein the formulation furher comprises an effective amount of naltrexone.

10. The method of claim 8 wherein the matrix is a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

11. The method of claim 8 wherein the matrix comprises release modifying agents.

12. The method of claim 8 wherein the polymer is polycyanoacrylate.

13. The method of claim 8 wherein the matrix releases in the stomach as a function of low pH.

14. The method of claim 8 wherein the matrix comprises a mucosal adhesive which enhances uptake in the gastrointestinal tract.

15. A method for making a controlled release formulation of an alcohol deterrent comprising encapsulating a cyanamide or salt thereof in a polymeric matrix in nanoparticulate or microparticulate form releasing the encapsulated cyanamide or salt thereof over a period of greater than four hours in the gastrointestinal tract in an amount effective to deter alcohol ingestion, and combining the cyanamide or salt thereof and polymeric matrix with a pharmaceutically acceptable carrier for oral administration.

16. The method of claim 15 further comprising encapsulating the cyanamide or salt thereof and polymeric matrix in an enteric coating.

* * * * *